United States Patent [19]

Gubitosa et al.

[11] Patent Number: 5,464,802
[45] Date of Patent: Nov. 7, 1995

[54] PROCESS FOR PREPARING A SUPPORTED METAL CATALYST FOR THE SELECTIVE HYDROGENATION OF HYDROCARBONS BY MEANS OF SUCH A PROCESS AND PROCESS FOR SELECTIVE HYDROGENATION OF HYDROCARBONS USING SUCH A CATALYST

[75] Inventors: Giuseppe Gubitosa, Novara; Alberto Cremona, Cusano Milanino, both of Italy

[73] Assignee: Ministero Dell'Universita' E Della Ricerca Scientifica E Tecnologica, Rome, Italy

[21] Appl. No.: 52,249

[22] Filed: Apr. 23, 1993

[30] Foreign Application Priority Data

Apr. 23, 1992 [IT] Italy .................................. MI92A0967

[51] Int. Cl.[6] .......................... B01J 31/00; B01J 27/122; B01J 23/72
[52] U.S. Cl. .......................... 502/331; 502/170; 502/225
[58] Field of Search .................................... 502/331, 170, 502/225

[56] References Cited

U.S. PATENT DOCUMENTS

| | | | |
|---|---|---|---|
| 3,932,548 | 1/1976 | Rausch | 502/331 |
| 3,953,368 | 4/1976 | Sinfelt | 502/331 |
| 4,101,451 | 7/1978 | Frevel et al. | 502/331 |
| 4,654,321 | 3/1987 | Pesa et al. | 502/331 |

FOREIGN PATENT DOCUMENTS

| | | |
|---|---|---|
| 2416210 | 2/1978 | France. |
| 3312252 | 10/1984 | Germany. |

*Primary Examiner*—Anthony McFarlane
*Assistant Examiner*—E. D. Irzinski
*Attorney, Agent, or Firm*—Rogers & Wells

[57] ABSTRACT

A process for preparing a supported metal catalyst based on Pd and Cu for the selective hydrogenation of polyunsaturated hydrocarbons comprises, in cascade, the steps of impregnating a porous support with a solution of a palladium and potassium salt, submitting the resulting solid product to a hydrogen flowing stream, impregnating the resulting solid material with a copper salt solution, submitting the resulting solid product to a flowing hydrogen stream, and drying the resulting solid product.

11 Claims, No Drawings

PROCESS FOR PREPARING A SUPPORTED METAL CATALYST FOR THE SELECTIVE HYDROGENATION OF HYDROCARBONS BY MEANS OF SUCH A PROCESS AND PROCESS FOR SELECTIVE HYDROGENATION OF HYDROCARBONS USING SUCH A CATALYST

The present invention relates to a process for preparing a palladium-based supported metal catalyst, in particular for the selective hydrogenation of hydrocarbons.

More particularly, the present invention relates to a catalyst for the selective hydrogenation of polyunsaturated hydrocarbons in order to yield hydrocarbons containing a same number of carbon atoms but having a higher H/C ratio ranging within desired limits.

Another aspect of the present invention relates to a method for hydrogenating $C_2$–$C_{30}$ alkynes and dienes in order to yield the corresponding olefins in which the double bond between carbon atoms is sited in the central portion of the molecule of the same olefin.

Therefore, in such a reaction of diene and/or alkyne hydrogenation, also an isomerization of the double bond of the produced mono-ene takes place.

The supported metal catalysts find uses in a wide, range of industrial processes. They are generally required to display high activity and selectivity values. Furthermore, the noble metal based catalyst obviously require high investment costs. Therefore, for the latter catalyst type, the trend is of using noble metal concentrations which are as low as possible consistently with the required catalytic performance. A decrease in metal concentration must be compensated for by a higher dispersion level on the support, i.e., by a decrease in average size of metal crystallites. Unfortunately, with decreasing average metal crystallite size, as known, the possibility of formation, of beta-phase palladium hydrate decreases during the course of the hydrogenation reaction, with a consequent decrease in catalyst selectivity.

Independently on whether the hydride phase will be formed or less, the smaller aggregates of supported metal display a higher affinity for unsaturated substrate molecules (dienes, alkynes, alkenes), owing to the presence, inside the interior of said aggregates, of electron-deficient metal species, with more or less stable metal-substrate complexes being consequently formed at the catalyst surface, which cause a sharp decrease in the activity of the latter.

A further problem relates to the fact that the carrier on which the metal is dispersed is not inert towards the hydrogenation reaction reactants and products. In particular, alumina-based carriers display, on their surface, acidic sites of Lewis and Bronsted types. Such sites may display parallel reactions to the hydrogenation reactions activated by the metal function, e.g., reactions of the type of dimerization and oligomerization of the unsaturated compounds present in the reactants and in the reaction products, with solid residues being consequently formed on the catalyst, which lead to catalyst quenching and/or to an increase in pressure drops inside the reactor due to catalytic bed clogging. Due to such a reason, to the alumina carriers, during their production, alkali-metal oxides are generally added and the resulting treated carriers are then submitted to calcination in order to stabilize them in the desired form. Such a methodology leads however to carriers being formed which display unsatisfactory morphological characteristics owing to the well-known phenomena of alumina sintering, during the course of thermal treatment, induced by alkali-metal oxides.

The present Applicant has surprisingly found now that by suitably combining palladium, copper and alkali-metal on a porous carrier, a catalyst can be obtained which displays high activity, selectivity and stability characteristics when said catalyst is used in the selective hydrogenation of hydrocarbons feedstock.

The process for preparing the catalyst according to the present invention comprises the following steps, in cascade:
(a) impregnating a porous support with a palladium and potassium salt solution,
(b) submitting the solid material obtained from the step (a) to a flowing hydrogen stream,
(c) impregnating the solid material obtained from the step (b) with a solution of a copper salt,
(d) submitting the solid material obtained from the step (c) to a flowing hydrogen stream, and
(e) drying the resulting solid product.

The palladium and potassium salt preferably used in the step of carrier impregnation is $K_2PdCl_4$, the copper salt is $Cu(HCOO)_2$. Furthermore, between the (b) and (c) steps, and between the (d) and (e) steps, the solid material is preferably submitted to a flowing inert gas stream.

Thanks to the above disclosed procedure, a selective deposition of metal palladium and copper on the carrier is obtained. The mechanism of selective deposition of the metal onto the support is thought to be the following.

By means of the first reduction under a flowing hydrogen stream palladium hydride is obtained which, by means of the subsequent treatment with inert gas, e.g., nitrogen, is partially transformed into metal palladium finely dispersed on the surface of the carrier. Palladium hydride still present on carrier surface makes it possible, in the step (c) of treatment with copper salt, the latter salt to be reduced and Cu to be deposited onto the carrier. An excessively high surface concentration of Pd hydride would lead to an unproper distribution of copper on the catalyst, so treating the carrier with an inert gas before impregnating it with copper solution, is preferred. The subsequent treatment with hydrogen is used in order to secure a complete reduction of the metal species deposited on the support. The optional further treatment with an inert gas aims hence at restoring the desired physical state of the metal component.

The use of copper-(II) formate as the copper salt offers the advantage that on the carrier no undesired anions are left which could interfere with the species present on the same carrier; in fact, during the carrier impregnation, the formate is decomposed with carbon dioxide being developed.

Preferably, before being impregnated with the $K_2PdCl_4$ solution, the carrier is impregnated with an HCl solution having a predetermined acidity in order that the palladium compound only permeates a surface layer of the carrier.

According to another preferred feature of the present invention, the conditions of treatment of the solid material (temperature and time) with hydrogen and with the inert gas, are substantially the same, because, should the treatment time with the inert gas be shorter than the hydrogen treatment time, the complete transformation would not be secured of palladium hydride into metal Pd.

The concentration of the solution of $Cu(HCOO)_2$, relatively to the amount of carrier to be impregnated, is such that a Cu concentration is obtained in the catalyst, which preferably is comprised within the range of from 0.01 to 0.2% by weight.

In order to prevent any undesired phenomena of formation of acidic sites by adsorbed anions, between the above said (a) and (b) steps, the carrier is preferably washed with distilled water or with a weakly alkaline solution ($K_2CO_3$).

As the carrier, alumina, silica, aluminosilicates, fossil meal, barium sulfate or activated charcoal may be used;

preferred is the use of gamma-alumina with a specific surface area comprised within the range of from 100 to 250 m²/g (as measured according to B.E.T. methodology), and with a total pore volume comprised within the range of from 0.4 to 0.7 cm³/g. The support may be in the form of balls, pellets, extruded shapes, or, preferably, as ring-shaped bodies.

The catalyst produced according to the present invention is particularly suitable for hydrogenating polyunsaturated hydrocarbons in general and, in particular the dienic and acetylenic compounds contained in gasolines from cracking. The catalyst obtained according to the present invention makes it possible $C_2$–$C_{30}$ alkines and dienes to be selectively hydrogenated in order to yield the corresponding mono-olefins. During the course of the hydrogenation, also a partial isomerization of the double bond in the produced mono-olefins occurs.

The high values of activity and selectivity of the catalyst according to the present invention are supposed to derive also from the particular distribution of metals on carrier surface, jointly with such crystallite sizes as to prevent that problems may arise which derive from the higher probability that, during the course of the hydrogenation reaction, palladium hydride of beta-phase is formed (with consequent decrease in catalyst selectivity), and from too small crystallite sizes which, by displaying a greater affinity for unsaturated molecules, may cause more or less stable metal-substrate complexes to be formed on catalyst surface, causing a sharp decrease of the activity of the latter.

The particular composition of the catalyst, containing from 0.05 to 0.4% of Pd, from 0.01 to 0.06% of Cu and from 0.01 to 3% of K, makes it possible high performance to be obtained in terms of activity, selectivity and stability, when said catalyst is used in the selective hydrogenation of hydrocarbon feedstock. In particular, by selecting potassium as the third metal the higher oxidation statuses of palladium are rendered more labile during the course of catalyst reduction and the formation is decreased of carbonaceous deposits (coke) on the same catalyst during the course of the hydrogenation reaction.

Further characteristics of the methodology of catalyst production according to the present invention will be evident from the following examples, which shall not be understood as being limitative of the scope of the present invention.

EXAMPLE 1

0.4 cm³ of a stoichiometric solution of $H_2PdCl_4$ containing 0.1 g of Pd/ml is collected and is diluted to approximately 20 cm³ with distilled water. 7.5 cm³ of 0.1M KOH are added and the pH value is measured; it should be of about 2.7. With a few droplets of a 0.1M KOH solution, the pH value is stabilized at about 4. The pH value of the solution is decreased down to 2 by adding 0.02N HCL. In such a way, a solution of $K_2PdCl_4$ is obtained, to be used for carrier impregnation, without precipitation problems. 20 g of gamma-alumina are then impregnated with the minimal amount of 0.02N HCL.

The gamma-alumina used displays the following characteristics:

| | | |
|---|---|---|
| Specific surface area (B.E.T.) | = | 178 m²/g |
| Total pore volume | = | 0.58 cm³/g |
| True specific weight | = | 3.32 cm³/g |
| Bulk specific weight | = | 1.13 cm³/g |

-continued

| | | |
|---|---|---|
| Bulk density, compacted | = | 0.54 cm³/g |
| Axial breaking strength | = | 20 kg/pellet |
| Rings De × Di × h | = | 5 × 2.5 × 5 mm |

De = outer diameter
Di = inner diameter
h = height

The mother solution of palladium is charged to the percolator which contains the carrier, thermostatted at 25° C. The solution is first allowed to percolate on the carrier until its level reaches the limit of bed dipping, then, after thoroughly mixing the bed three or four times, is recirculated for 2.5 hours. Such a rather long time period was selected in order to be sure that the interaction of the palladium compound with the carrier is complete; subsequent tests demonstrated that times of 30–45 minutes are already enough in order that a complete interaction may be obtained.

After such a time period, the recirculation is discontinued; the mother solution is clear and colourless and has a slightly higher pH value than 4. The support is washed with a solution prepared with 20 cm³ of a 1M solution of $K_2CO_3$ diluted to 100 cm³ with distilled water at a temperature of 60° C. For that purpose, 2.5 liters of distilled water are used and the test for chlorides is carried out on the last wash liquors, which must yield a negative result. Through the support, a flowing hydrogen stream is then flown for 1.5 hours, at a temperature of 60° C.

The hydrogen flow is discontinued and the solid material is washed with 1 litre of distilled water, with the chloride test being carried out again on the last wash liquors, which must yield a negative result. Then, through the carrier a stream of nitrogen is flown at a temperature of 60° C., during 1.5 hours. The flow is interrupted and 0.93 cm³ of a solution of $Cu(HCOO)_2$ containing 0.0107 g of Cu/ml, diluted to 50 cm³ with distilled water, is recirculated.

This operation is carried out under an inert nitrogen atmosphere at 25° C., for 2 hours and 15 minutes. Then, through the carrier a hydrogen stream and then a nitrogen stream are flown, in each case at 60° C. and for 1.5 hours. The resulting product is discharged from the percolator and is charged to an oven, inside which it is heated at a temperature of 120° C. for 3 hours. The catalyst contains 0.2% of Pd, 0.3% of Cu and 0.41% of K (weight % values based on catalyst weight).

EXAMPLES 2–6

The same methodology as of Example 1 was followed, with the only difference that the amount of $Cu(HCOO)_2$ solution containing 0.0107 g of Cu/ml, and consequently the Cu amount in the catalyst, were varied. The solution amount used and the relevant Cu content in the catalyst are reported in the following Table (the Pd content is identical to that as of Example 1).

| | cm³ of $Cu(HCOO)_2$ solution containing 0.0107 g of Cu/cm³ | Cu %, based on catalyst weight |
|---|---|---|
| Example 2 | 47.0 | 2.27 |
| Example 3 | 33.6 | 1.47 |
| Example 4 | 3.70 | 0.17 |
| Example 5 | 0.37 | 0.01 |

-continued

| | cm³ of Cu(HCOO)₂ solution containing 0.0107 g of Cu/cm³ | Cu %, based on catalyst weight |
|---|---|---|
| Example 6 | 0.19 | 0.007 |

EXAMPLE 7

The operating procedure is identical to that as of Example 1 up to the first reduction of the solid material with hydrogen. Then, a solution is caused to recirculate for 2.5 hours, which contains 0.03 g of CuCl₂ dihydrate dissolved in 20 cm³ of 0.02N HCl and diluted to 100 cm³ with distilled water (pH=2.5), at the temperature of 25° C. At the end of the impregnation, the solution has a pH value of 4.4 and is clear and colourless. The support is washed with a solution prepared with 20 cm³ of a 1M solution of K₂CO₃ diluted to 100 cm³ with distilled water, at a temperature of 60° C. For that purpose, 2 liters of distilled water are used and the test for chlorides is carried out on the last washing liquors, which must yield a negative result. Then, through the carrier a hydrogen stream is flown at a temperature of 60° C. for 1.5 hours. The hydrogen flow is discontinued and the solid material is washed twice with an alkaline solution of the above disclosed type. On the last wash liquors, the test for chlorides is carried-out again, which must yield a negative result. A nitrogen stream is flown at the temperature of 60° C. for 3 hours. The catalyst, discharged from the percolator and charged to an oven for 3 hours at the temperature of 120° C., contains 0.2% of Pd, 0.03% of Cu and 1.9% of K (weight % values based on catalyst weight).

EXAMPLE 8 (COMPARISON EXAMPLE)

The initial procedure is identical to that as of Example 1, up to the impregnation with the Pd mother solution and subsequent washing with a diluted K₂CO₃ solution.

Then, through the resulting solid product a nitrogen stream is flown at a temperature of 60° C. for 2 hours. The solid material is washed 8 times with alkaline solutions of the above disclosed type and on the last washing liquors the test for chloride is carried out, which much yield a negative result. Then, a nitrogen stream is flown through the solid material at a temperature of 25° C. for 10 hours and then at 60° C. for 2 hours. The catalyst, discharged from the percolator and charged to an oven for 4 hours at 120° C., contains 0.2% by weight of Pd and 1.72% by weight of K.

CATALYTIC TESTS

The catalytic tests were carried out on the reaction of isoprene hydrogenation in liquid phase under atmospheric pressure. The isothermal reactor is fed from bottom upwards with hydrogen and with a mixture of isoprene at 5% (by volume) in n-heptane. The operating conditions of the catalytic test are as follows: 6.7 g of catalyst constituted by bodies of industrial size (see Example 1) are diluted (1:8 by weight) with ring-shaped bodies of an inert material (steatite) of an analogous size. The hydrogen flow rate is 3.3 Nl/h, isoprene flow rate is 3.0 cm³/h and the LHSV (liquid hourly space velocity) value is of 4.8 h⁻¹. The temperature, which is constant throughout the catalytic bed, is 28° C.

During the course of each catalytic test, at regular intervals and over defined times, the reaction products are collected for gas chromatographic analysis. Isoprene (2-methyl-1,3-butadiene) was selected as the model reactant, because it is a diene with such characteristics as to make it possible the activity, selectivity and isomerization power of a hydrogenation catalyst to be evaluated.

The possible products from the isoprene hydrogenation reaction are 3-methyl-1-butene, 2-methyl-1-butene, 2-methyl-2-butene and isopentane. The latter is the undesired reaction product and on it the evaluation of catalyst selectivity is based on it.

The performances of each of the catalysts prepared according to Examples 1–8 were compared to those of an industrial catalyst (MO3S produced and traded by Montecatini Tecnologic S.p.A.) containing 0.3% by weight of palladium.

In the following Table (in which the catalysts are designated by means of the same number as of the Example relevant to their preparation), the catalysts performances are reported in terms of activity (expressed as the ratio of catalyst activity to the standard activity×100) and selectivity (expressed as the ratio of catalyst selectivity to the standard selectivity×100).

| | Pd % | Cu % | K % | Activity % | Selectivity % |
|---|---|---|---|---|---|
| Catalyst 1 | 0.2 | 0.03 | 0.41 | 153 | 120 |
| Catalyst 2 | 0.2 | 2.27 | 0.05 | 84 | 140 |
| Catalyst 3 | 0.2 | 1.47 | 0.06 | 95 | 120 |
| Catalyst 4 | 0.2 | 0.17 | 0.05 | 111 | 120 |
| Catalyst 5 | 0.2 | 0.01 | 0.3 | 144 | 100 |
| Catalyst 6 | 0.2 | 0.007 | 0.97 | 120 | 120 |
| Catalyst 7 | 0.2 | 0.03 | 1.90 | 156 | 80 |
| Catalyst 8 | 0.2 | — | 1.72 | 135 | 120 |

From the preceding table, it clearly results that, the activity value displays a maximum peak with copper content varying. The best results in terms of activity and selectivity were achieved with the catalyst manufactured according to Example 1.

The catalyst according to Example 7 yielded an extremely good activity value, but a slight decrease in selectivity.

We claim:

1. Process for preparing a Pd and Cu-containing catalyst for the selective hydrogenation of polyunsaturated hydrocarbons, wherein said process comprises the following sequential steps:

(a) impregnating a porous support with a palladium and potassium salt solution, (b) submitting the solid material obtained from the step (a) to a flowing hydrogen stream, (c) impregnating the solid material obtained from the step (b) with a solution of a copper salt, (d) submitting the solid material obtained from the step (c) to a flowing hydrogen stream, (e) and drying the resulting solid product, with the proviso that the resulting catalyst comprises from 0.05% to 0.4% by weight Pd, from 0.01% to 0.2% by weight Cu, and from 0.01% to 3% by weight K.

2. Process according to claim 1, wherein the Pd and K salt is K₂PdCl₄.

3. Process according to claim 2, wherein said Cu salt is Cu(HCOO)₂.

4. Process according to claim 2, wherein said Cu salt is CuCl₂.

5. Process according to claim 1, wherein between the (b) and (c) steps and the (d) and (e) steps, the solid material is submitted to a flowing-inert gas stream.

6. Process according to claim 2, wherein before being impregnated with the solution of $K_2PdCl_4$, the carrier is impregnated with an HCl solution.

7. Process according to claim 5, wherein the conditions of carrier treatment with hydrogen and with said inert gas respectively are substantially identical.

8. Process according to claim 1, wherein between said (a) and (b) steps, the carrier is washed with water or with a solution comprised of potassium carbonate.

9. Process according to claim 1, wherein said carrier is gamma-alumina having a specific surface area comprised within the range of from 100 to 250 $m^2/g$ (B.E.T.).

10. Process according to claim 9, wherein the total volume of the pores is comprised within the range of from 0.4 to 0.7 $cm^3/g$.

11. A supported metal catalyst consisting of a porous carrier having deposited thereon from 0.05 to 0.4% of Pd, from 0.01 to 0.06% of Cu and from 0.01 to 3% of K, and capable of selectively hydrogenating polyunsaturated hydrocarbons.

* * * * *